(12) United States Patent
Cheng et al.

(10) Patent No.: US 10,234,442 B2
(45) Date of Patent: Mar. 19, 2019

(54) DEVICE AND METHOD FOR FINDING CELL NUCLEUS OF TARGET CELL FROM CELL IMAGE

(71) Applicant: METAL INDUSTRIES RESEARCH & DEVELOPMENT CENTRE, Kaohsiung (TW)

(72) Inventors: Ming-Hui Cheng, Kaohsiung (TW); Yan-Jun Chen, Kaohsiung (TW); Tsung-Chih Yu, Kaohsiung (TW); Bo-Wei Pan, Kaohsiung (TW); Chun-Sen Wu, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 178 days.

(21) Appl. No.: 15/363,543

(22) Filed: Nov. 29, 2016

(65) Prior Publication Data
US 2017/0309017 A1 Oct. 26, 2017

(30) Foreign Application Priority Data
Apr. 26, 2016 (TW) .............................. 105112999 A

(51) Int. Cl.
*G06T 7/00* (2017.01)
*G01N 33/483* (2006.01)
(Continued)

(52) U.S. Cl.
CPC ..... *G01N 33/4833* (2013.01); *G01N 15/1475* (2013.01); *G06T 7/12* (2017.01);
(Continued)

(58) Field of Classification Search
CPC .... G06T 7/12; G06T 7/66; G06T 7/70; G06T 7/90; G06T 5/30; G06T 5/001;
(Continued)

(56) References Cited

U.S. PATENT DOCUMENTS

| 7,907,769 | B2 * | 3/2011 | Sammak | ............ | G06K 9/00127 |
| | | | | | 382/133 |
| 2005/0266395 | A1 * | 12/2005 | Gholap | .............. | G01N 33/5091 |
| | | | | | 435/4 |

(Continued)

*Primary Examiner* — Yon J Couso
(74) *Attorney, Agent, or Firm* — Volpe and Koenig, P.C.

(57) ABSTRACT

The present invention discloses a method for finding a cell nucleus of a target cell from a cell image, wherein the cell image includes the target cell and at least one variation cell, and the target cell includes cytoplasm and the cell nucleus. The method includes steps of: (a) processing the cell image via an image processor such that the cytoplasm, the cell nucleus and the variation cell have different shades of color; (b) demarcating the outlines of the cytoplasm, the cell nucleus and the variation cell; (c) calculating geometrical reference points of the outlines; (d) calculating the distances from the geometrical reference point of the cytoplasm outline to the geometrical reference point of the cell nucleus outline and to the geometrical reference points of the variation cell outlines; and (e) finding a specific geometrical reference point having a shortest distance to locate a specific outline corresponding to the specific geometrical reference point as the cell nucleus.

17 Claims, 7 Drawing Sheets
(2 of 7 Drawing Sheet(s) Filed in Color)

(51) Int. Cl.
*G01N 15/14* (2006.01)
*G06T 7/12* (2017.01)
*G06T 7/66* (2017.01)
*G01N 15/10* (2006.01)
*G01N 15/00* (2006.01)

(52) U.S. Cl.
CPC ........ *G06T 7/66* (2017.01); *G01N 2015/0065* (2013.01); *G01N 2015/1006* (2013.01); *G06T 2207/10056* (2013.01); *G06T 2207/30024* (2013.01)

(58) Field of Classification Search
CPC ... G06T 7/13; G06T 7/60; G06T 2207/30024; G06T 2207/10056; G01N 15/1475; G01N 2015/0065; G01N 2015/1006; G01N 33/4833
See application file for complete search history.

(56) References Cited

U.S. PATENT DOCUMENTS

| | | | | |
|---|---|---|---|---|
| 2009/0190821 A1* | 7/2009 | Marugame | ......... | G06K 9/00127 382/133 |
| 2010/0098317 A1* | 4/2010 | Kiyuna | ................ | G06T 7/0012 382/133 |
| 2014/0227682 A1* | 8/2014 | Seth | ........................ | C12Q 1/70 435/5 |

\* cited by examiner

DEVICE AND METHOD FOR FINDING CELL NUCLEUS OF TARGET CELL FROM CELL IMAGE

CROSS-REFERENCE TO RELATED APPLICATION AND CLAIM OF PRIORITY

The application claims the benefit of Taiwan Patent Application No. 105112999, filed on Apr. 26, 2016, at the Taiwan Intellectual Property Office, the disclosures of which are incorporated herein in their entirety by reference.

FIELD OF THE INVENTION

The present invention is related to a device and a method to find a cell nucleus from a cell image. Particularly, the present invention is related to a device and a method to exclude inflamed cells and find a cell nucleus from a cell image.

BACKGROUND OF THE INVENTION

Human Papillomavirus (HPV), a DNA virus, belongs to the Papillomaviridae family and the Papillomavirus genus, and mainly infects human epidermis and mucosa tissues. About 170 types of HPV have been identified, wherein some types cause warts and cancers after invading the human body, but others do not cause any symptoms. Some research indicates that 99.7% of cervical cancer is caused by HPV infection.

According to a report from the World Health Organization (WHO), cervical cancer is the second most common cancer in women in the world. According to statistics from the Ministry of Health and Welfare, the Executive Yuan, Taiwan, the annual incidence rate of cervical cancer in Taiwan is 27 cases per 100,000 women, and the age-standardized mortality rate of cervical cancer is 9.18 persons per 100,000 cases. More than 1,000 women on average die from cervical cancer per year; that is, 3 women die from cervical cancer per day. Therefore, there needs to be pathology detection for cervical cancer to determine whether pathological variations occur in the cervical cancer cells.

Pathology detection worldwide was valued at about US$1.98 billion in 2012, and will increase to US$5.7 billion in 2020, indicating that the compound growth rate is as much as 14.3%. The compound growth rate in the Asia-Pacific market, which leapt to the highest in the world, is 22.2%, and the Asia-Pacific area has become the area with the most market potential for development. The compound growth rate in North America and Europe is 79%, and North America and Europe are the most common areas which use digital pathology detection and identification. The global pathology detection market is classified into Whole Slide Imaging (WSI), Image Analysis-Informatics & Storage, and Communication and Integrated Platforms, wherein WSI has the largest market demand. Thus, the growth of global pathology screening and diagnostic systems is faster than expected. Because the specimens for the pathology screening were entirely analyzed and observed one by one by medical technicians in the past and the speed cannot keep up with the increasing growth rate and the increasing number of Pap smears, a system that would benefit pathologists to analyze and identify pathology detection and fully satisfy clinical needs and market expectations, and would solve the technician shortage and overstrain problems for doctors and pathologists.

In general, malignant cervical cancer cells may deform, whereas the cell nucleus becomes larger, and thus cellular characteristic parameters may be analyzed to determine whether the cervical cells are malignant. The cellular characteristic parameters include the cell nuclear-cytoplasmic radius ratio, cell nuclear-cytoplasmic area ratio, cell nuclear morphology, cell membrane morphology and cell density in stain, etc. For example, the cell nucleus of a malignant cell becomes larger causing its cell nuclear-cytoplasmic radius (or area) ratio to be larger than that of a normal cell, and thus a cell where its nuclear-cytoplasmic ratio has become larger is determined to be a malignant cell. The current pathology screening system is a method where an image of cervical cells is segmented, the cellular characteristics are calculated and the malignancy of the cells is classified. However, a great deal of noise exists in the images of the actual Pap smears, where the size and the color of inflamed cells are the most similar to those of the cell nucleus of the cervical cells, and it is easy to mistake these inflamed cells as the cell nucleus of the cervical cells when retrieving the outline of the nucleus. Furthermore, this process leads to errors in the cellular segmentation and characteristics calculation, and causes irregular determination results after the cellular malignancy classification. For instance, as shown in FIG. 1(a), there are no inflamed cells in an ideal image of the cellular specimen, and the cell nucleus of the cervical cell can be clearly identified. However, there must be some inflamed cells in the female's ostium vagina. The inflamed cells neighboring the female's ostium vagina together with the cervical cells are sampled during the Pap smear sampling. The image characteristics of these inflamed cells are highly similar to those of the cell nucleus of the cervical cell, and these inflamed cells are either outside of the cytoplasm of the cervical cell (as shown in FIG. 1(b)) or inside the cytoplasm of the cervical cell (as shown in FIG. 1(c)). Therefore, to a digital image software identification system, it is easy to misidentify the inflamed cells dispersed inside the cytoplasm of the cervical cell as the cell nucleus of the cervical cell. In addition, if the inflamed cells are not excluded, the system may define all inflamed cells as a cell nucleus to analyze the cellular characteristic parameters (such as the nuclear-cytoplasmic ratio). Subsequently, the system may calculate areas or radiuses of all inflamed cells to enlarge the nuclear-cytoplasmic ratio and misjudge the cells as malignant cells or abnormal cells when calculating the nuclear-cytoplasmic ratio. Accordingly, to avoid this misjudgment, the system needs to exclude the noise (such as a disturbance from the inflamed cells) in the cell image, to increase the accuracy of the system during the cervical cell screening.

To overcome the disadvantages above, it is ideal to have a new digital pathologic screening and diagnostic device and method. It is therefore the Applicant's attempt to deal with the many limitations in the prior art.

SUMMARY OF THE INVENTION

To avoid a mistake where the inflamed cells are misjudged as the cell nucleus when demarcating the cell nucleus outline, the present invention discloses a demarcation method to automatically exclude the inflamed cells using the position of an outline demarcation region and color analysis, such that the identification system can demarcate the correct position of the cell nucleus, and the accuracy of the cell characteristic calculation and the identification of the malignancy classification are improved.

In accordance with one aspect of the present disclosure, a device for finding a cell nucleus of a target cell from a cell image is disclosed, wherein the cell image includes a cytoplasm region and plural dark regions. The device includes: a cytoplasm outline demarcation unit demarcating a cytoplasm outline from the cell image; a dark region outline demarcation unit coupled to the cytoplasm outline demarcation unit and demarcating plural dark region outlines from the cell image; an image processor coupled to the cytoplasm outline demarcation unit and the dark region outline demarcation unit, and processing images of the cytoplasm outline and the plural dark region outlines; a barycenter calculation unit coupled to the image processor and calculating a cytoplasm outline barycenter of the cytoplasm outline and dark region outline barycenters of respective dark region outlines; a distance calculation unit coupled to the barycenter calculation unit and calculating distances between the cytoplasm outline barycenter and respective dark region outline barycenters; and a determination unit coupled to the distance calculation unit, and finding a shortest distance from the calculated distances to locate a specific dark region outline barycenter having the shortest distance, and a specific dark region corresponding to the specific dark region outline barycenter as the cell nucleus.

In accordance with another aspect of the present disclosure, a method for finding a cell nucleus from a cell image is disclosed, wherein the cell image includes a cytoplasm region, a cell nucleus region and plural dark regions. The method includes steps of: (a) demarcating a cytoplasm outline from the cell image via a cytoplasm outline demarcation unit; (b) demarcating plural dark region outlines from the cell image via a dark region outline demarcation unit; (c) processing respective images of the cytoplasm outline and the dark region outlines via an image processor; (d) calculating a cytoplasm outline barycenter of the cytoplasm outline and dark region outline barycenters of respective dark region outlines via a barycenter calculation unit; (e) calculating distances between the cytoplasm outline barycenter and respective dark region outline barycenters via a distance calculation unit; and (f) finding a shortest distance from the calculated distances to locate a specific dark region outline barycenter having the shortest distance, and a specific dark region corresponding to the specific dark region outline barycenter as the cell nucleus via a determination unit.

In accordance with one more aspect of the present disclosure, a method for finding a cell nucleus of a target cell from a cell image, wherein the cell image includes the target cell and at least one variation cell, and the target cell includes a cytoplasm and the cell nucleus. The method includes steps of: (a) processing the cell image via an image processor such that the cytoplasm, the cell nucleus and the variation cell have different shades of color; (b) demarcating respective outlines of the cytoplasm, the cell nucleus and the variation cell via a demarcation unit; (c) calculating barycenters of respective outlines via a geometrical reference point calculation unit; (d) calculating respective distances from the barycenter of the cytoplasm outline to the barycenter of the cell nucleus outline and to the barycenters of the variation cell outlines via a distance calculation unit; and (e) finding a specific barycenter having a shortest distance determined from the respective distances from the barycenter of the cytoplasm outline to the barycenter of the cell nucleus outline and to the barycenters of the variation cell outlines to locate a specific outline corresponding to the specific barycenter as the cell nucleus via a determination unit.

In accordance with one more aspect of the present disclosure, a method for finding a cell nucleus of a target cell from a cell image is disclosed, wherein the cell image includes the target cell and at least one variation cell, and the target cell includes cytoplasm and the cell nucleus. The method includes steps of: (a) processing the cell image via an image processor such that the cytoplasm, the cell nucleus and the variation cell have different shades of color; (b) demarcating respective outlines of the cytoplasm, the cell nucleus and the variation cell via a demarcation unit; (c) calculating geometrical reference points of respective outlines via a geometrical reference point calculation unit; (d) calculating respective distances from the geometrical reference point of the cytoplasm outline to the geometrical reference point of the cell nucleus outline and to the geometrical reference points of the variation cell outlines via a distance calculation unit; and (e) finding a specific geometrical reference point having a shortest distance determined from the respective distances from the geometrical reference point of the cytoplasm outline to the geometrical reference point of the cell nucleus outline and to the geometrical reference points of the variation cell outlines to locate a specific outline corresponding to the specific geometrical reference point as the cell nucleus via a determination unit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1A:
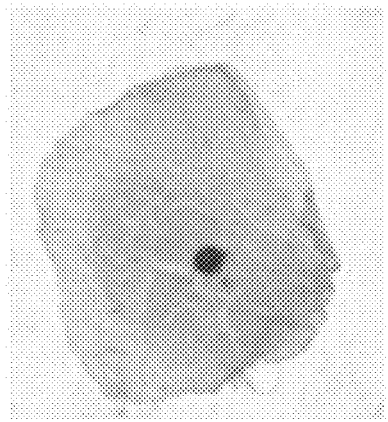
FIG. 1(a) is a Pap smear cell image without inflamed cells in the prior art.
Figure 1B:
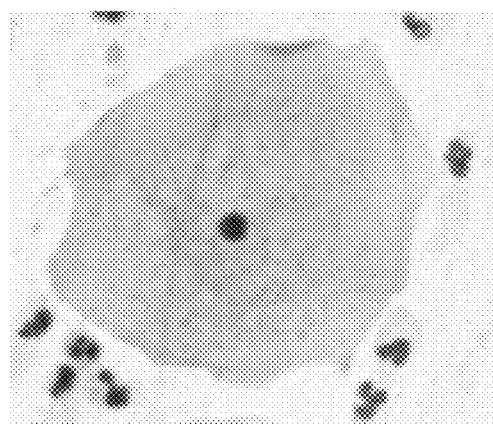
FIG. 1(b) is a Pap smear cell image showing inflamed cells dispersed outside of the cytoplasm in the prior art.
Figure 1C:
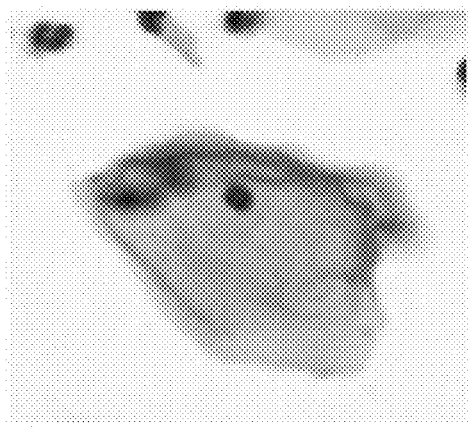
FIG. 1(c) is a Pap smear cell image showing inflamed cells dispersed inside the cytoplasm in the prior art.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed. In the preferred embodiments, the same reference numeral represents the same element in each embodiment.

In various embodiments, the present invention discloses a system and a method to determine the position of a cell nucleus of a cell from a cell image. An identification system is used in the present invention to demarcate the positions of regions and analyze colors of those regions, and exclude the inflamed cells to find the position of the cell nucleus by calculating the barycenters of the individual regions and the distances between the barycenters, so that the accuracy of the cell characteristic calculation and the identification of the malignant classification improve.

The cellular sample in the present invention may be obtained and treated using common or regular sampling methods (such as a Pap smear), and then a cell image showing a single cell is retrieved from the treated cellular sample using photomicrography. Inflamed cells, the cytoplasm and the cell nucleus of the single cell are present in a regular cell image. Because the size and the color of the inflamed cells and the cell nucleus are similar in the cell image and their colors are usually darker, the inflamed cells and the cell nucleus are defined as the dark regions, and the cytoplasm is defined as the cytoplasm region. Any variant cells (such as inflamed cells) which may be defined as the dark regions in the cell image are the objects that the identification system excludes in the present invention.

Figure 2:
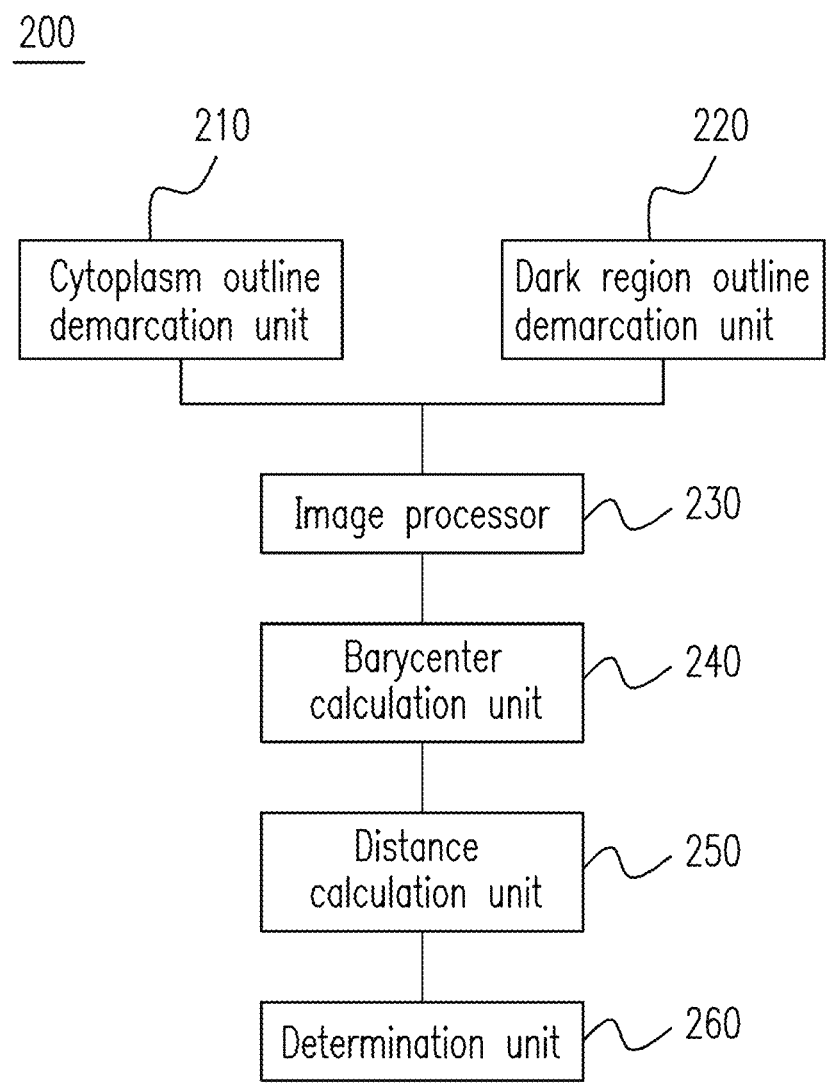
FIG. 2 is a schematic diagram showing a cell nucleus identification system in the present invention.
Figure 3:
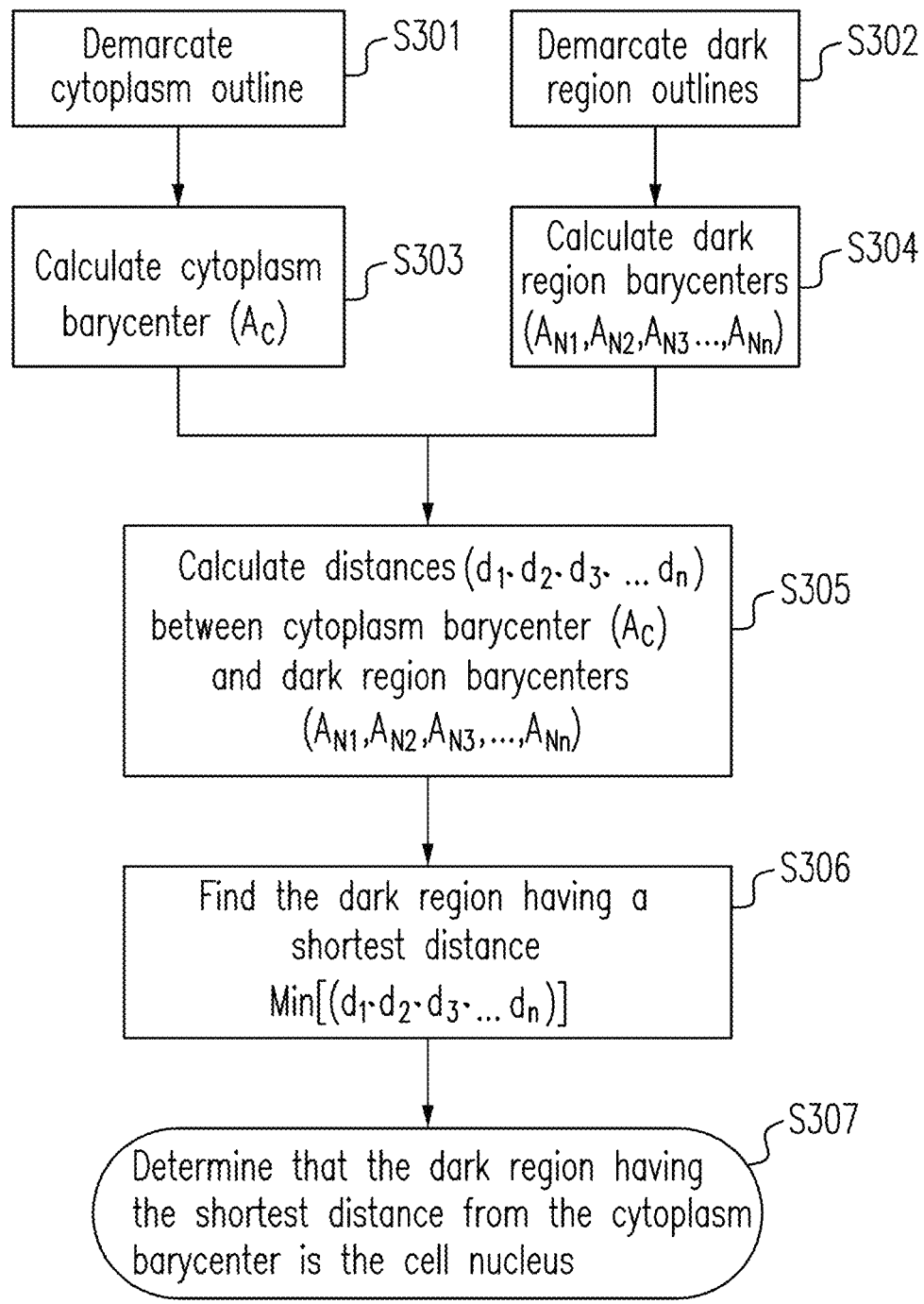
FIG. 3 is a schematic diagram showing a cell nucleus identification method in the present invention.

Please refer to FIGS. 2 and 3, which respectively are schematic diagrams showing the cell nucleus identification system and method in the present invention. The cell nucleus identification system 200 of the present invention includes a cytoplasm outline demarcation unit 210, a dark region outline demarcation unit 220, an image processor 230, a barycenter calculation unit 240, a distance calculation unit 250 and a determination unit 260.

After obtaining the cell image, the cytoplasm outline demarcation unit 210 is used to demarcate a cytoplasm outline of the cytoplasm of the cell (Step 301 in FIG. 3), and the dark region outline demarcation unit 220 is used to demarcate dark region outlines of the dark regions, i.e. the cell nucleus of the cell and the inflamed cells (Step 302 in FIG. 3). The method for demarcating the cytoplasm outline and the dark region outlines are respectively shown in FIGS. 4 and 5.

Figure 4:
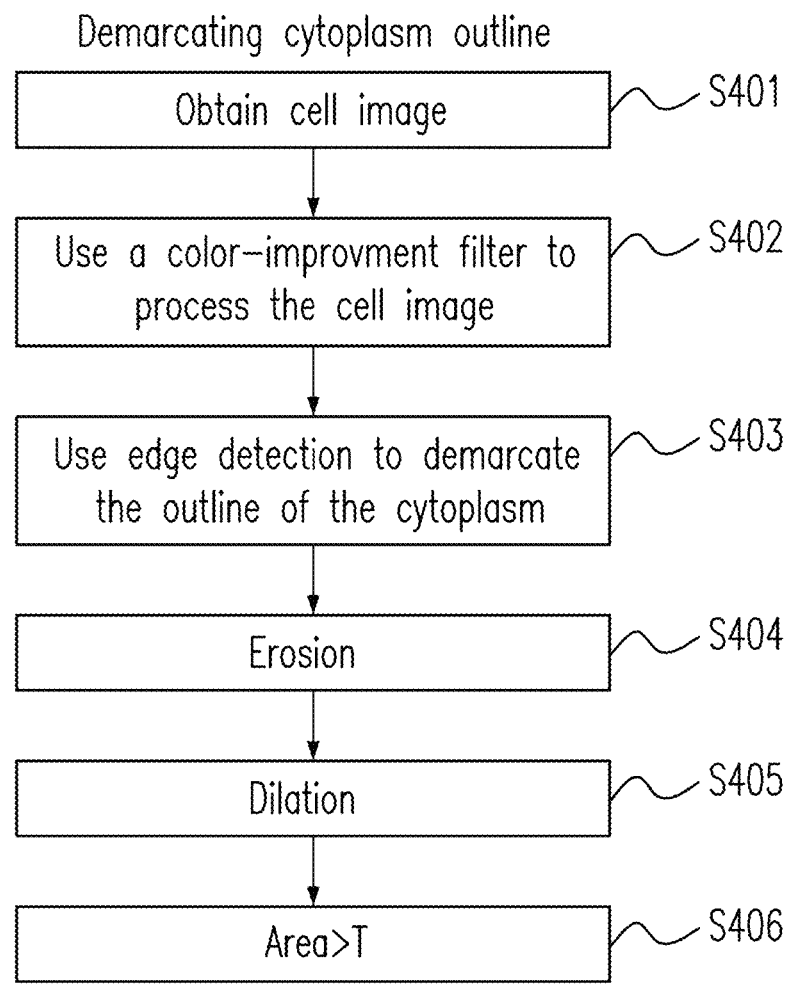
FIG. 4 is a schematic diagram showing a method for demarcating the outline of cytoplasm in the present invention.
Figure 6A:
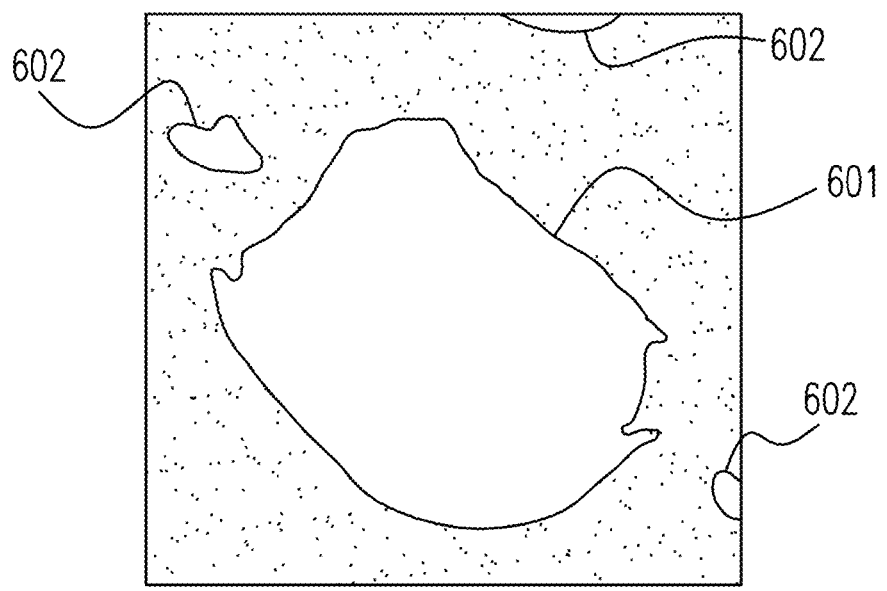
FIG. 6(a) is a schematic diagram showing the cytoplasm outline of the cell image after the image processing in the present invention.

Please refer to FIG. 4, which is a schematic diagram showing a method for demarcating the outline of cytoplasm in the present invention. After obtaining the cell image (Step 401), a color-improvement filter is used to process the cell image (Step 402) to enhance an edge of the cell, increase the color and contrast ratio of the cell image, and de-emphasize the dark regions. Subsequently, an edge detection method is used to demarcate the outline of the cytoplasm (Step 403) to obtain a preliminary cytoplasm outline. The image processor 230 is used to process the preliminary cytoplasm outline using one or more than one erosion and dilation (Steps 404 and 405) to more completely demarcate the outline of the cytoplasm and obtain the cytoplasm outline. In one embodiment, as shown in FIG. 6(a), a cytoplasm outline 601 is demarcated from a cell image containing inflamed cells using the method for demarcating the cytoplasm outline. When the demarcation of the cytoplasm outline is finished, the variety of regions may be demarcated from the cell image. The areas of these regions are calculated by the cytoplasm outline demarcation unit 210, and a specific region where the area is larger than a threshold (T) such as 500 pixels is selected (Step 406). In FIG. 6(a), the outlines having the smaller areas 602 are excluded after Step 406.

The color-improvement filter and the edge detection method are conventional techniques in the art, and any method where the edge may be detected and the color and contract ratio of the image may be enhanced falls within the scope of the present invention. In another embodiment, the color-improvement filter includes, but is not limited to, a bilateral filter, a mean filter and a Gaussian smoothing filter. The edge detection method includes, but is not limited to, a Sobel operator, a watershed algorithm and a snake algorithm. A Laplacian filter, Sobel filter, Prewitt filter or Roberts filter can also be used to perform the edge detection.

Figure 5:
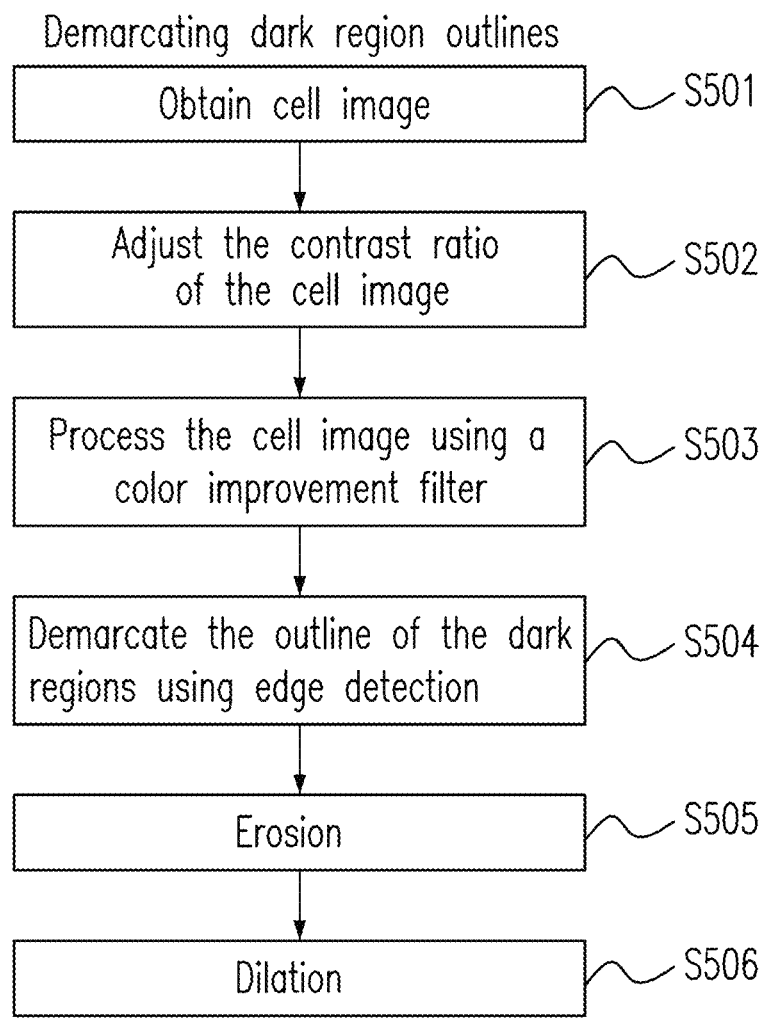
FIG. 5 is a schematic diagram showing a method for demarcating the outline of dark regions in the present invention.
Figure 6B:
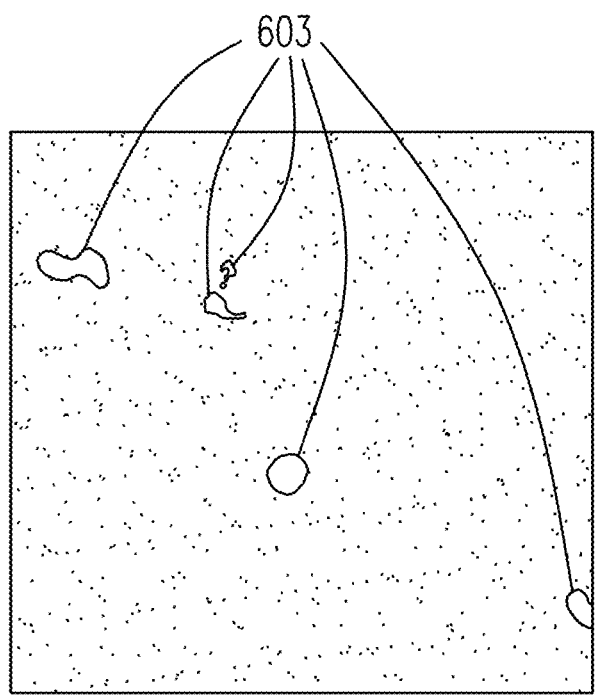
FIG. 6(b) is a schematic diagram showing the dark region outlines of the cell image after the image processing in the present invention.

Please refer to FIG. 5, which is a schematic diagram showing a method for demarcating the outline of dark regions in the present invention. After obtaining the cell image (Step 501), an image processing method for Histogram equalization or log transformation is used to adjust the contrast ratio of the cell image (Step 502), and then a color-improvement filter is used to process the cell image (Step 503) to emphasize the dark regions which may be the cell nucleus, increase the color and contrast ratio of the cell image, and de-emphasize the cytoplasm (the light region). Next, an edge detection method is used to demarcate the outline of the dark regions (Step 504) to obtain a preliminary dark region outline. The image processor 230 is used to process the preliminary dark region outline using one or more than one erosion and dilation (Steps 505 and 506) to complete the demarcation of the outlines of the dark regions and obtain the dark region outlines. In one embodiment, as shown in FIG. 6(b), the dark region outlines 603 are obtained by demarcating the inflamed cells in the cell image using the method for demarcating the outline of the dark regions.

Figure 7A:
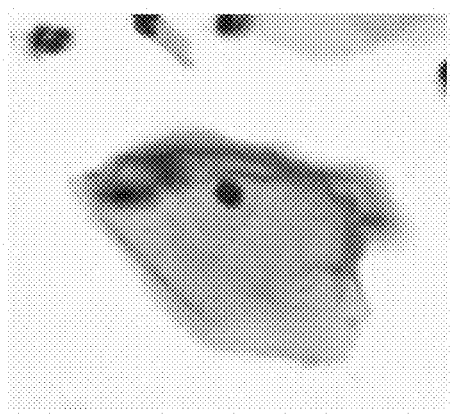
FIG. 7(a) is an image showing the cervical cell in the present invention.
Figure 7B:
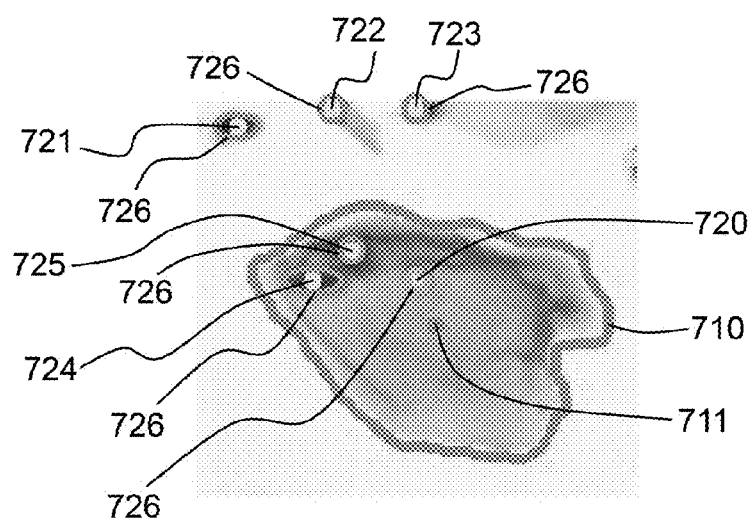
FIG. 7(b) is a schematic diagram showing the image of the cervical cell in the present invention, wherein the individual barycenters of the cytoplasm outline and the dark region outlines are calculated.

After the cytoplasm outline and the dark region outlines are demarcated using the cytoplasm outline demarcation unit 210, the dark region outline demarcation unit 220 and the image processor 230, the barycenter calculation unit 240 calculates the barycenter coordinates for all pixels in the cytoplasm outline and the dark region outlines to obtain a cytoplasm barycenter ($A_c$) and plural dark region barycenters ($A_{N1}, A_{N2}, A_{N3} \ldots A_{Nn}$) which may be the cell nucleus (Step 303 and Step 304 in FIG. 3). Similarly, the method for calculating the barycenter of the present invention is a conventional technique in the art. In one embodiment, an image of a cervical cell is shown in FIG. 7(a). Please refer to FIG. 7(b), which is a schematic diagram showing the image of the cervical cell in the present invention, wherein the individual barycenters of the cytoplasm outline and the dark region outlines are calculated. In FIG. 7(b), the cytoplasm outline 710 and dark region outlines 726 are obtained after demarcating the image of the cervical cell using the cytoplasm outline demarcation unit 210 and the dark region outline demarcation unit 220, and the cytoplasm barycenter 711 and dark region barycenters 720-725 are obtained after calculating the pixels in the cytoplasm outline 710 and the dark region outlines 726. In another embodiment, other geometrical reference points (such as the axis center, the center, etc.) of the cytoplasm and dark regions also can be used to locate the cell nucleus of the cell.

After calculating the cytoplasm barycenter and the dark region barycenters, the distance calculation unit 250 calculates the distance between the cytoplasm barycenter and the individual dark region barycenters to obtain a distance $d_1$ between the cytoplasm barycenter $A_c$ and the dark region barycenter $A_{N1}$, a distance $d_2$ between the cytoplasm barycenter $A_c$ and the dark region barycenter $A_{N2}$, a distance $d_3$ between the cytoplasm barycenter $A_c$ and the dark region barycenter $A_{N3}$, . . . , and a distance $d_n$, between the cytoplasm barycenter $A_c$ and the dark region barycenter $A_{Nn}$. Similarly, the method for calculating the distances in the present invention is a conventional technique in the art. In one embodiment, the calculation method for distances is the calculation method for Euclidean distance. In one embodiment, as shown in FIG. 7(b), the distance calculation unit 250 calculates the distances between the cytoplasm barycenter 710 and the individual dark region barycenters 720-725. For example, the distance between the cytoplasm barycenter 710 and the dark region barycenter 720 is $d_1$, the distance between the cytoplasm barycenter 710 and the dark region barycenter 721 is $d_2$, the distance between the cytoplasm barycenter 710 and the dark region barycenter 722 is $d_3$, the distance between the cytoplasm barycenter 710 and the dark region barycenter 723 is $d_4$, the distance between the cytoplasm barycenter 710 and the dark region barycenter 724 is $d_5$, and the distance between the cytoplasm barycenter 710 and the dark region barycenter 725 is $d_6$.

Figure 7C:
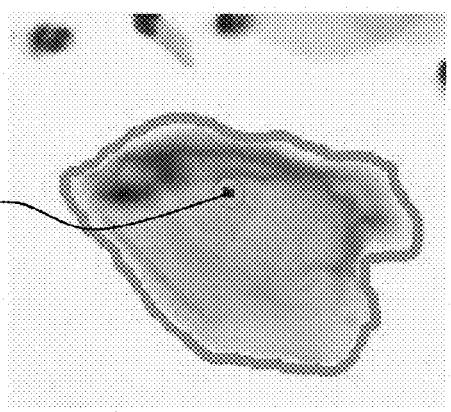
FIG. 7(c) is a schematic diagram showing the image of the cervical cell in the present invention, wherein the position of the cell nucleus is identified using the identification system of the present invention.

Finally, the determination unit 260 compares the lengths of these distances ($d_1$, $d_2$, $d_3$ . . . $d_n$) and finds the shortest distance linked to the cytoplasm barycenter (Min[($d_1$, $d_2$, $d_3$ . . . $d_n$)]) (referring to Step 306 in FIG. 3). Next, the determination unit 260 determines that the dark region having the shortest distance to the cytoplasm barycenter is the cell nucleus of the cell (Step 307 in FIG. 3). In one embodiment, the determination unit 260 finds that the distance $d_1$ has the shortest length among the distances $d_1$-$d_6$, and determines that the distance $d_1$ is the distance between the cytoplasm barycenter 710 and the dark region barycenter 720. Thus, as shown in FIG. 7(c), the determination unit 260 determines that the dark region corresponding to the dark region outline barycenter 720 is represented by the distance $d_1$ as the cell nucleus of the cervical cell in the cell image.

Embodiments

1. A device for finding a cell nucleus of a target cell from a cell image, including: a cytoplasm outline demarcation unit demarcating a cytoplasm outline from the cell image; a dark region outline demarcation unit coupled to the cytoplasm outline demarcation unit and demarcating plural dark region outlines from the cell image; an image processor coupled to the cytoplasm outline demarcation unit and the dark region outline demarcation unit, and processing images of the cytoplasm outline and the plural dark region outlines; a barycenter calculation unit coupled to the image processor and calculating a cytoplasm outline barycenter of the cytoplasm outline and dark region outline barycenters of respective dark region outlines; a distance calculation unit coupled to the barycenter calculation unit and calculating distances between the cytoplasm outline barycenter and respective dark region outline barycenters; and a determination unit coupled to the distance calculation unit, and finding a shortest distance from the calculated distances for locating a specific dark region outline barycenter having the shortest distance, and a specific dark region corresponding to the specific dark region outline barycenter as the cell nucleus.

2. The device according to Embodiment 1, wherein the cell image is an image of a single cell, and the cell image is an image of a cervix cell.

3. The device according to any one of Embodiments 1 or 2, wherein the image processor processes the images of the cytoplasm outline and the dark region outlines using an erosion and a dilation.

4. The device according to any one of Embodiments 1 to 3, wherein the cytoplasm outline demarcation unit and the dark region outline demarcation unit demarcate the cytoplasm outline and the plural dark region outlines using one selected from a group consisting of a Sobel operator, a watershed algorithm and a snake algorithm, and the distance calculation unit calculates the distances using an Euclidean distance.

5. A method for finding a cell nucleus from a cell image, including: (a) demarcating a cytoplasm outline from the cell image via a cytoplasm outline demarcation unit; (b) demarcating plural dark region outlines of plural dark regions from the cell image via a dark region outline demarcation unit; (c) processing respective images of the cytoplasm outline and the dark region outlines via an image processor; (d) calculating a cytoplasm outline barycenter of the cytoplasm outline and dark region outline barycenters of respective dark region outlines via a barycenter calculation unit; (e) calculating distances between the cytoplasm outline barycenter and respective dark region outline barycenters via a distance calculation unit; and (f) finding a shortest distance from the calculated distances to locate a specific dark region outline barycenter having the shortest distance, and a specific dark region corresponding to the specific dark region outline barycenter as the cell nucleus via a determination unit.

6. The method according to Embodiment 5, wherein the cell image is captured using photomicrography.

7. The method according to Embodiment 5 or 6, wherein the images of the cytoplasm outline and the dark region outlines are processed using an erosion and a dilation.

8. The method according to any one of Embodiments 5 to 7, wherein step (a) further includes: (a1) preprocessing the cell image via the image processor by using a bilateral filter to increase a contrast ratio of the cell image.

9. The method according to any one of Embodiments 5 to 8, wherein step (b) further includes: (b1) preprocessing the cell image via the image processor by using a bilateral filter to increase a contrast ratio of the cell image; and (b2) using one of a histogram equalization method and a log transformation method to enhance the plural dark regions.

10. The method according to any one of Embodiments 5 to 9, wherein in the step (d), the cytoplasm outline barycenter and the dark region outline barycenters are calculated based on pixels inside the cytoplasm outline and the dark region outlines.

11. A method for finding a cell nucleus of a target cell from a cell image, wherein the cell image includes the target cell and at least one variation cell, and the target cell includes a cytoplasm and the cell nucleus, including: (a) processing the cell image via an image processor such that the cytoplasm, the cell nucleus and the variation cell have different shades of color; (b) demarcating respective outlines of the cytoplasm, the cell nucleus and the variation cell via a demarcation unit; (c) calculating barycenters of respective outlines via a geometrical reference point calculation unit; (d) calculating respective distances from the barycenter of the cytoplasm outline to the barycenter of the cell nucleus outline and to the barycenters of the variation cell outlines via a distance calculation unit; and (e) finding a specific barycenter having a shortest distance determined from the respective distances from the barycenter of the cytoplasm outline to the barycenter of the cell nucleus outline and to the barycenters of the variation cell outlines to locate a specific outline corresponding to the specific barycenter as the cell nucleus via a determination unit.

12. The method according to Embodiment 11, wherein the cytoplasm has a first color shade, and the cell nucleus and the variation cell have a second color shade after the cell image is processed.

13. A method for finding a cell nucleus of a target cell from a cell image, wherein the cell image includes the target cell and at least one variation cell, and the target cell includes cytoplasm and the cell nucleus, including: (a) processing the cell image via an image processor such that the cytoplasm, the cell nucleus and the variation cell have different shades of color; (b) demarcating respective outlines of the cytoplasm, the cell nucleus and the variation cell via a demarcation unit; (c) calculating geometrical reference points of respective outlines via a geometrical reference point calculation unit; (d) calculating respective distances from the geometrical reference point of the cytoplasm outline to the geometrical reference point of the cell nucleus outline and to the geometrical reference points of the variation cell outlines via a distance calculation unit; and (e) finding a specific geometrical reference point having a shortest distance determined from the respective distances from the geometrical reference point of the cytoplasm outline to the geometrical reference point of the cell nucleus outline and to the geometrical reference points of the variation cell outlines to locate a specific outline corresponding to the specific geometrical reference point as the cell nucleus via a determination unit.

What is claimed is:

1. A device for finding a cell nucleus of a cervix cell from a cervix cell image, wherein the cell image comprises a cytoplasm region and plural dark regions, the plural dark regions comprise a cell nucleus region and at least one inflamed cell region, and a color of the plural dark regions is darker than that of the cytoplasm region, the device comprising:
a cytoplasm outline demarcation unit demarcating a cytoplasm outline from the cervix cell image;
a dark region outline demarcation unit coupled to the cytoplasm outline demarcation unit and demarcating plural dark region outlines from the cervix cell image;
an image processor coupled to the cytoplasm outline demarcation unit and the dark region outline demarcation unit, and processing images of the cytoplasm outline and the plural dark region outlines;
a barycenter calculation unit coupled to the image processor and calculating a cytoplasm outline barycenter of the cytoplasm outline and dark region outline barycenters of respective dark region outlines;
a distance calculation unit coupled to the barycenter calculation unit and calculating distances between the cytoplasm outline barycenter and respective dark region outline barycenters; and
a determination unit coupled to the distance calculation unit, and finding a shortest distance from the calculated distances for locating a specific dark region outline barycenter having the shortest distance, and a specific dark region corresponding to the specific dark region outline barycenter as the cell nucleus of the cervix cell,
wherein the device determining whether the cervix cell is a cancerous cell by analyzing a cell characteristic calculation of the cell nucleus of the cervix cell.

2. The device as claimed in claim 1, wherein the cervix cell image is an image of a single cell.

3. The device as claimed in claim 1, wherein the image processor processes the images of the cytoplasm outline and the dark region outlines using an erosion and a dilation.

4. The device as claimed in claim 1, wherein the cytoplasm outline demarcation unit and the dark region outline demarcation unit demarcate the cytoplasm outline and the plural dark region outlines using one selected from a group consisting of a Sobel operator, a watershed algorithm and a snake algorithm, and the distance calculation unit calculates the distances using an Euclidean distance.

5. A method for finding a cell nucleus of a cervix cell from a cervix cell image, wherein the cervix cell image comprises a cytoplasm region and plural dark regions, the plural dark regions comprise a cell nucleus region and at least one inflamed cell region, and a color of the plural dark regions is darker than that of the cytoplasm region, the method comprising:
(a) demarcating a cytoplasm outline from the cervix cell image via a cytoplasm outline demarcation unit;
(b) demarcating plural dark region outlines from the cervix cell image via a dark region outline demarcation unit;
(c) processing respective images of the cytoplasm outline and the dark region outlines via an image processor;
(d) calculating a cytoplasm outline barycenter of the cytoplasm outline and dark region outline barycenters of respective dark region outlines via a barycenter calculation unit;
(e) calculating distances between the cytoplasm outline barycenter and respective dark region outline barycenters via a distance calculation unit; and
(f) finding a shortest distance from the calculated distances to locate a specific dark region outline barycenter having the shortest distance, and a specific dark region corresponding to the specific dark region outline barycenter as the cell nucleus of the cervix cell via a determination unit,
wherein a cell characteristic calculation of the cell nucleus of the cervix cell is analyzed to determine whether the cervix cell is a cancerous cell.

6. The method as claimed in claim 5, wherein the cervix cell image is captured using photomicrography.

7. The method as claimed in claim 5, wherein the images of the cytoplasm outline and the dark region outlines are processed using an erosion and a dilation.

8. The method as claimed in claim 5, wherein the step (a) further comprises:
(a0) preprocessing the cervix cell image via the image processor by using one selected from a group consisting of a bilateral filter, a mean filter and a Gaussian smoothing filter to increase a contrast ratio of the cervix cell image.

9. The method as claimed in claim 5, wherein the step (b) further comprises:
(b0) preprocessing the cervix cell image via the image processor by using one selected from a group consisting of a bilateral filter, a mean filter and a Gaussian smoothing filter to increase a contrast ratio of the cervix cell image, and then using one of a histogram equalization method and a log transformation method to enhance the plural dark regions.

10. The method as claimed in claim 5, wherein the cytoplasm outline barycenter and the dark region outline barycenters are calculated based on pixels inside the cytoplasm outline and the dark region outlines.

11. A method for finding a cell nucleus of a cervix cell from a cervix cell image, wherein the cervix cell image comprises the cervix cell and at least one inflamed cell, and the cervix cell comprises a cytoplasm and the cell nucleus, the method comprising:

(a) processing the cervix cell image via an image processor such that the cytoplasm has a shade of color different from that of the cell nucleus and the inflamed cell;
(b) demarcating respective outlines of the cytoplasm, the cell nucleus and the inflamed cell via a demarcation unit;
(c) calculating geometrical reference points of respective outlines via a geometrical reference point calculation unit;
(d) calculating respective distances from the geometrical reference point of the cytoplasm outline to the geometrical reference point of the cell nucleus outline and to the geometrical reference points of the inflamed cell outlines via a distance calculation unit; and
(e) finding a specific geometrical reference point having a shortest distance determined from the respective distances from the geometrical reference point of the cytoplasm outline to the geometrical reference point of the cell nucleus outline and to the geometrical reference points of the inflamed cell outlines to locate a specific outline corresponding to the specific geometrical reference point as the cell nucleus via a determination unit,
wherein a cell characteristic calculation of the cell nucleus of the cervix cell is analyzed to determine whether the cervix cell is a cancerous cell.

12. The method as claimed in claim 11, wherein the cytoplasm has a first color shade, and the cell nucleus and the inflamed cell have a second color shade after the cell image is processed.

13. The method as claimed in claim 12, wherein the cytoplasm is processed using one selected from a group consisting of a bilateral filter, a mean filter and a Gaussian smoothing filter such that the cytoplasm has the first color shade.

14. The method as claimed in claim 12, wherein the cell nucleus and the inflamed cell are processed using one selected from a group consisting of a bilateral filter, a mean filter and a Gaussian smoothing filter, and then using one of a histogram equalization method and a log transformation method such that the cell nucleus and the inflamed cell have the second color shade.

15. The method as claimed in claim 11, wherein the outlines are demarcated using one selected from a group consisting of a Sobel operator, a watershed algorithm and a snake algorithm.

16. The method as claimed in claim 11, wherein the step (b) further comprises:
(b1) processing each outline using an erosion and a dilation via the image processor.

17. The method as claimed in claim 11, wherein the geometrical reference point is a barycenter of the outlines.

* * * * *